United States Patent [19]
Kramer

[11] Patent Number: 6,120,774
[45] Date of Patent: Sep. 19, 2000

[54] HETEROPHIL-ADAPTED POULTRY VACCINE

[75] Inventor: Theodore T. Kramer, Ames, Iowa

[73] Assignee: Iowa State University Research Foundation, Inc., Ames, Iowa

[21] Appl. No.: 08/801,722

[22] Filed: Feb. 14, 1997

Related U.S. Application Data

[63] Continuation of application No. PCT/US96/20555, Dec. 18, 1996, abandoned.
[60] Provisional application No. 60/009,644, Dec. 19, 1995.
[51] Int. Cl.$^7$ ............................. A61K 39/02; A01N 63/00
[52] U.S. Cl. .................................... 424/234.1; 424/258.1; 424/93.1; 424/93.2; 424/93.4; 435/245; 435/822; 435/879
[58] Field of Search ............................. 424/258.1, 184.1, 424/234.1, 237.1, 241.1, 244.1, 257.1, 93.1, 93.2, 93.4, 93.42, 93.44, 93.48; 435/243, 245, 822, 848, 849, 882, 885, 879

[56] References Cited

U.S. PATENT DOCUMENTS

| | | |
|---|---|---|
| 4,472,378 | 9/1984 | Shuster et al. . |
| 5,356,797 | 10/1994 | Niesel et al. . |
| 5,387,744 | 2/1995 | Curtiss, III et al. . |
| 5,436,001 | 7/1995 | Kramer . |
| 5,538,729 | 7/1996 | Czinn et al. . |

FOREIGN PATENT DOCUMENTS

| | | |
|---|---|---|
| 0 648 502 A1 | 4/1993 | European Pat. Off. . |
| 0 650 733 A1 | 3/1995 | European Pat. Off. . |

OTHER PUBLICATIONS

Roof et al. Am J. Vet. Res. 1992, vol. 53, No. 8, 13 28–32.
Kramer et al. Am J. Vet Res. 1992. vol. 53, No. 4, 444–8.
Koehler 1993 93rd General Meeting. Am Soc. Microbiol abstract only.

Molina et al. Infection & Immunity.1988, vol. 30, No. 1, 224–30.

Hickman CP, et al., Integrated Principles of Zoology, 7th Edition, Times Mirror/Mosby College Publishing Chapter 26: The Birds, pp. 600–603, 605–606 (1984).

Andreasen CB et al., "Cytochemical Staining Characteristics of Chicken Heterophils and Eosinophils," *Veterinary Clinical Pathology*, 19(2):51–53 (1990).

Andersson E., et al., "The Role of Propeptide for Processing and Sorting of Human Myeloperoxidase," *J. Biological Chemistry*, 273(8): 4747–4753 (1998).

Birrenkott G. et al. in Avian Hematology—Heterophils, Clemson University@ http://agweb.clemson.edu/poultry/bld/hetero.html (1995).

Bloom and Fawcett: A Textbook of Histology, DW Fawcett, Chapman and Hall, New York, pp. 112 and 118 (1994).

Proceedings of the Symposium on the Diagnosis and Control of Salmonella, San Diego, California, Oct. 29, 1991, p. 27, Abstract.

Research on Salmonellosis in the Food Safety Consortium, United States Animal Health Association, Little Rock, Arkansas, Oct. 17, 1996, 4 pages.

*Primary Examiner*—Patricia A. Duffy
*Attorney, Agent, or Firm*—Fish & Richardson P.C., P.A.

[57] ABSTRACT

A method for vaccinating poultry to prevent salmonellosis and other microbial-related health problems in humans is described. The method involves isolation of a poultry heterophil-adapted strain of a microorganism that may be used in a vaccine. A vaccine comprising a preparation of the poultry heterophil-adapted strain is administered to poultry to reduce the transmission of microorganisms causing salmonellosis and other illnesses.

27 Claims, 5 Drawing Sheets

HETEROPHIL-ADAPTED POULTRY VACCINE

This application is a continuation of PCT Patent Application No. PCT/US96/20555, filed Dec. 18, 1996, now abandoned which claims priority to U.S. Provisional Patent Application No. 60/009,644, filed Dec. 19, 1995.

FIELD OF THE INVENTION

This invention relates to a vaccine for poultry to prevent salmonellosis and other microorganism-related health problems in humans. In particular, this invention relates to use of a heterophil-adapted strain of microorganism to vaccinate poultry.

BACKGROUND OF THE INVENTION

Salmonellosis is caused by a group of gram negative bacteria from the genus Salmonella, and is responsible for approximately 2 million cases of food poisoning annually in the United States. Salmonellosis caused by *Salmonella enteritidis* (SE) in eggs has been the most important food-born public health Salmonella hazard.

Most outbreaks have been traced to consumption of insufficiently cooked eggs. A number of phage types of SE exist but the majority of outbreaks have been traceable to a single or a few phage types of SE. Human SE food poisoning epidemics have also been reported from many other countries, but the phage types reported have not necessarily been those prevailing in the United States.

Some avian strains of SE are vertically transmitted to the eggs of laying hens. The ovaries, oviduct and isthmus have been identified as sites of vertical transmission. In addition, some observations have pointed to cloacal infection of the egg. It is not known which strains or phage types of SE are vertically transmitted, and genetic or molecular requirements for vertical transmission are not known. Infection of hens with SE has led to colonization of the ceca and of the reproductive organs, usually without disease. In most instances infected hens have continued to lay eggs at normal frequencies. Because of absence of overt disease, infection has been difficult to detect clinically or by serologic diagnostic procedures.

Detection of SE in the hen house, individual hens and/or eggs is a difficult task, with a high degree of uncertainty. In the absence of total eradication of infection, vaccination remains the method of choice for disease control. Because SE does not usually cause disease in hens, there is not a vigorous immune response, and hens remain carriers for long periods, even for life. Therefore, it is presumed that immunization will have to be repeatedly administered. Only live attenuated vaccines given orally can be expected to be efficacious in salmonellosis. Curtiss, R. III, et al., *Vet. Microbiol.* 37: 397–405 (1993). It is possible that a vaccine strain may have to displace the egg-transmitted strain in the gut and possibly the reproductive tract of hens.

Salmonellosis due to SE is in most instances not a poultry disease but one of the most serious public health hazards worldwide. Prevention of the risk of SE transmission from ingested eggs would save several thousands of lives and would save around $1 billion annually. Thus, a vaccine for poultry against transmission of Salmonella would reduce occurrence of salmonellosis in humans and make a significant contribution to public health worldwide.

SUMMARY OF THE INVENTION

The present invention features a method of producing a heterophil-adapted strain of microorganism suitable for use as a live, attenuated vaccine in a poultry species. The method involves incubating wild-type microorganisms with a first population of heterophils taken from a member of a poultry species to generate a sample including heterophil-internalized microorganisms as well as extracellular microorganisms. A substantially pure clone of the heterophil-internalized microorganisms is used for the next step. Microorganisms from the heterophil-internalized clone are incubated with a second population of heterophils to form a next passage of heterophil-internalized microorganisms and a next passage of extracellular microorganisms. Preferably the second population of heterophils is taken from the same member of the poultry species as was used in the first passage. These procedures are repeated until at least three passages, and preferably at least five passages, are completed. A substantially pure clone of the heterophil-internalized microorganisms from the last passage is isolated to obtain a heterophil-adapted strain. The heterophil-adapted strain can be, although is not necessarily, arginine hydrolase negative.

The poultry species to which this invention is applicable include, without limitation, turkeys, guinea fowl, pigeons, quail, partridge, broiler chickens, and laying hens. The species of microorganism can include members of the genus Salmonella, for example *Salmonella enteritidis*.

In a preferred embodiment, isolation of a substantially pure clone of heterophil-internalized microorganism includes incubating the heterophils with an antibiotic, washing, then disrupting the heterophils to release the internalized microorganisms. The heterophils may be incubated with more than one antibiotic. Antibiotics useful in the methods of the present invention preferably include, without limitation, aminoglycosides, or aminocyclitols. Most preferable is the use of kanamycin and gentamicin. The antibiotics can be used individually, sequentially or in any combination effective for killing or inactivating the relevant extracellular microorganisms.

In another aspect, the invention features a method of vaccinating poultry by administering a preparation of a poultry heterophil-adapted strain of microorganism to poultry, preferably by an oral route of administration. In an alternative embodiment, both a poultry heterophil-adapted strain of microorganism and cholera toxin, a mucosal adjuvant, are provided to the poultry.

In a further aspect, the present invention involves a substantially pure poultry heterophil-adapted strain of microorganism. In preferred embodiments, the microorganism is a member of the genus Salmonella. Most preferably, the Salmonella genus member is *Salmonella enteritidis*. The heterophil-adapted strain can be arginine hydrolase negative.

In still another aspect, the present invention features a live, attenuated vaccine for poultry comprising a preparation of a substantially pure poultry heterophil-adapted strain of microorganism. In a preferred embodiment, the microorganism is a member of the genus Salmonella. More preferably, the member of the genus Salmonella is *Salmonella enteritidis*, for example *Salmonella enteritidis* strain SETK499, or strain SETK598 having ATCC Accession Number 55770 (The American Type Culture Collection; 12301 Parklawn Drive, Rockville, Md. 20852; Deposited: Apr. 26, 1994). In an alternative embodiment, the vaccine includes a preparation of a substantially pure poultry heterophil-adapted strain of microorganism as well as cholera toxin. Preferably, the vaccine is adapted for oral administration.

In another related aspect, the invention includes a poultry member comprising a poultry heterophil-adapted strain of microorganism. In a preferred embodiment, the microorganism is a member of the genus Salmonella, for example *Salmonella enteritidis*. In a further related aspect, the invention includes eggs and body parts (wings, breasts, drumsticks, or other body parts sold, for example, for human consumption) derived from the immunized poultry member. Such eggs and body parts are at a lower risk for microorganism contamination than are eggs and body parts derived from non-immunized but otherwise comparable poultry members.

DESCRIPTION OF THE PREFERRED EMBODIMENTS

The invention relates to a method of producing a heterophil-adapted strain suitable for use as a live, attenuated vaccine for poultry. Such strains are useful in reducing the incidence of food-born microorganisms, for example *Salmonella enteritidis* (SE), causing health problems in humans. Specifically, heterophil-adapted strains of SE have been isolated and administered orally to laying hens in order to immunize and prevent egg transmission of SE.

The term heterophil as used herein refers to polymorphonuclear or granulocytic cells in poultry blood. The term poultry as used herein refers to domesticated fowl including without limitation turkeys, guinea fowl, pigeons, quail, partridge, broiler chickens and laying hens. A poultry member as used herein refers to an individual member of a poultry species.

In general, the invention exploits the method of heterophil adaptation for obtaining vaccines comprising heterophil-adapted strains of microorganisms. In one aspect of the invention, a heterophil-adapted strain may be produced by incubating a wild-type strain of a microorganism with heterophils from a member of a poultry species. As used herein, the term "wild-type" refers to any microorganism that is not poultry heterophil-adapted. In a preferred embodiment, the poultry species is a laying hen. The microorganism can be, for example, any member of the genus Salmonella, including without limitation *Salmonella enteritidis* (SE), *Salmonella gallinarum* (SG), *Salmonella pullorum* (SP), *Salmonella dublin* (SD), and *Salmonella typhimurium* (ST). In a preferred embodiment, the microorganism used for heterophil adaptation is SE. Various SE strains may be employed as wild-type microorganisms used for heterophil adaptation, including without limitation wild-type SE strains SETK474 and SETK584.

Heterophil adaptation may be accomplished in various ways. For example, a wild-type strain of microorganism may be incubated with a first population of heterophils from a member of a poultry species until some of the microorganisms are internalized by the heterophils. Preferably, the microorganisms are incubated with heterophils for about 30 min. at about 41° C., although other incubation times may be suitable depending on incubation temperatures, species of poultry and microorganism, and other conditions. In any case, incubation times are selected to allow for internalization of at least some microorganisms by the heterophils. Such internalization may be readily monitored by bacteriologic cultures in GN broth and MacConkey agar of disrupted heterophils.

Incubation with heterophils may be performed using whole blood, preferably blood collected in a heparinized tube. Alternatively, purified or partially purified heterophils may be used. In a preferred embodiment, blood from a laying hen is collected in a heparinized tube and incubated with an overnight culture of the wild-type strain of microorganism. Following overnight incubation, the culture is adjusted to an optical density (O.D.) of about 0.2 at 595 nm in a McFarland nephelometer. Incubation of poultry heterophils with wild-type microorganisms generates a sample containing heterophil-internalized microorganisms as well as microorganisms that are not internalized (i.e., "extracellular" microorganisms) because of a ratio of about 10:1 of bacteria:heterophils. Thus, extracellular microorganisms as used herein refers to microorganisms on the outside surfaces of the heterophils or dispersed in the inoculation medium and unattached to the heterophils. Heterophil-internalized microorganisms as used herein refers to microorganisms that have been internalized by the heterophils during incubation.

The next step in heterophil adaptation involves isolation of a substantially pure clone of heterophil-internalized microorganisms. This involves, first, removal of extracellular microorganisms from the incubation mixture of heterophils and wild-type microorganisms. Any available method of removing extracellular microorganisms may be used. In a preferred embodiment, removal of extracellular microorganisms involves incubation with an antibiotic effective for killing or otherwise inactivating the extracellular microorganisms, followed by washing with media to remove the antibiotic from the sample. Incubation in the presence of an antibiotic should be long enough to kill or inactivate substantially all of the extracellular microorganisms. Preferably, incubation with an antibiotic is for about 60 min at about 41° C. The wild-type strain of the microorganism generally should be sensitive to the antibiotic used in order to kill or inactivate substantially all of the extracellular microorganisms. In a preferred embodiment, samples are incubated with kanamycin or gentamicin in order to destroy the extracellular microorganisms. In an alternative embodiment, extracellular microorganisms are killed or inactivated by sequentially incubating with more than one antibiotic. For example, the sample may be first incubated with kanamycin, followed by incubation with gentamicin. After exposure to antibiotic, the antibiotic is removed, for example by centrifugation at low speed to pellet the heterophils. The supernatant containing the antibiotic is removed and fresh medium is added to the pellet. The pellet may be resuspended by vortexing.

After killing or inactivating the extracellular microorganisms in the sample and removing any antibiotics, the heterophil-internalized microorganisms may be released by disruption of the washed heterophils. In a preferred embodiment, disruption of the heterophils is performed using a detergent such as saponin. Then, an aliquot of the disrupted heterophil sample is grown on agar plates or in liquid medium and subsequently plated on agar plates. In a preferred embodiment, an aliquot of about 6 drops of the disrupted heterophil sample is drop-plated on agar plates. Preferably, the agar plates are MacConkey agar plates. Following an appropriate period of growth, a single well-isolated colony from an agar plate is identified, and represents a substantially pure clone of heterophil-internalized microorganisms completing the first passage of heterophil adaptation.

In a second passage, a culture of the cloned heterophil-internalized microorganisms from the first passage is incubated with a second population of heterophils, preferably from the same source (i.e., the same bird) as used in the first passage, and is then taken through the same procedures as described above. Similarly, each subsequent passage is initiated by incubating heterophils from the same bird with a culture of the cloned heterophil-internalized microorganisms from the immediately preceding passage.

Heterophil adaptation of a microorganism may be done by starting with a wild-type microorganism and performing repeated passages of heterophil adaptation as described above. Preferably, a heterophil-adapted microorganism has been taken through at least three passages of heterophil adaptation, more preferably through at least four or five passages of heterophil adaptation, and even more preferably through at least six passages of heterophil adaptation. Heterophil adaptation may be considered successful when the number of colonies recovered after the detergent disruption of the heterophils diminishes from dozens of colonies in the first passage to about 2–5 colonies when plated on MacConkey agar. The diminished number of bacteria surviving in heterophils after each passage may be interpreted as reduced survivability in phagocytes.

A heterophil-adapted strain may exhibit a number of genetic or biochemical changes. For example, loss of arginine hydrolase may indicate that the heterophil-adapted strain has lost its capability to produce nitrous oxide (NO), an important oxidative toxic product. It has been learned recently that NO may be the key microbicidal substance in the killing of Salmonella by macrophages. Thus, in a preferred embodiment, the heterophil-adapted strain is arginine hydrolase negative. Loss of a virulence plasmid is another example of changes exhibited by some heterophil-adapted strains.

The heterophil-adapted strains can be used for vaccinating poultry. In order to vaccinate poultry, a vaccine comprising a preparation of the heterophil-adapted strain is administered. In a preferred embodiment, poultry are vaccinated by oral administration of a preparation of heterophil-adapted strain of microorganism. Preferably, oral administration is accomplished by adding a preparation of the heterophil-adapted strain to drinking water. In a preferred embodiment, a preparation of a heterophil adapted strain is added to about 50 mL of deionized drinking water. A drinking water cup is left in the cage until it is substantially empty in order to ensure administration of substantially all of the preparation. The preparation may be in the form of a culture, a frozen sample, a lyophilized sample, an agar stab or any other form appropriate for maintaining bacteria. In an alternative embodiment, cholera toxin (a mucosal adjuvant) is provided to the poultry, in addition to the heterophil-adapted microorganisms. In a preferred embodiment, the preparation contains on the order of about $10^6$ to about $10^8$ colony forming units (CFU's) for each bird of the heterophil-adapted strain as administered to the poultry.

The suitability of heterophil-adapted strains as live vaccines for poultry may be determined in experiments exposing poultry to wild-type challenge strains and to heterophil-adapted strains. Frequency and length of shedding, and egg transmissibility, of challenge strains after exposure to vaccine strains may be used as measures of vaccine efficacy. For example, fecal shedding and egg transmission patterns of vaccine and challenge strains before and after vaccination may be evaluated and compared to the same parameters in hens infected with challenge control strains.

In one set of experiments, laying hens were exposed to wild-type challenge strains by addition of the challenge strains to drinking water. After two rounds of exposure to challenge strains, the hens were exposed to a vaccine strain comprising a five-passage (5X) heterophil-adapted strain of SE. The hens were then exposed to challenge strains, then again to the vaccine strain. This set of experiments established that infection with wild-type challenge strains led to prolonged fecal shedding and egg transmission and that there was no convalescent immunity against fecal excretion and only partial convalescent immunity against egg transmission. The vaccine strain was shed at low frequency for a short time in feces and there was no egg transmission of the vaccine strain. Subsequent exposure of the vaccinated hens to wild-type challenge strains or to vaccine strains resulted in a reduction in frequency and duration of fecal shedding, and elimination of egg transmission.

In a second set of experiments, a six-passage (6X) heterophil-adapted strain was used as a vaccine strain. Laying hens were exposed to the vaccine strain at doses of $10^6$ or $10^8$ CFU's per bird followed by exposure to a wild-type challenge strain. A second group was exposed to a vaccine strain along with cholera toxin, a known mucosal adjuvant, followed by exposure to a challenge strain. These experiments demonstrated that low dose exposure does not result in fecal shedding, while administration of a high dose of vaccine strain results in some fecal shedding for a limited time (about 10 to 14 days). The use of cholera toxin reduced the amount of fecal shedding. The fecal shedding of the challenge strain was significantly lower in vaccinated groups when compared to a challenge control group (unvaccinated). Significantly, neither the vaccine strain nor the challenge strain could be isolated from eggs of the vaccinated groups. Repeated vaccinations with the vaccine strains reduced the level of fecal shedding of the challenge strain in immunized hens. These experiments indicated that heterophil-adapted strains are safe and effective as vaccines for poultry.

The invention will be further understood with reference to the following illustrative embodiments, which are purely exemplary, and should not be taken as limiting the true scope of the present invention as described in the claims.

EXAMPLE 1

Heterophil Adaptation of Wild-Type Salmonella Enteritidis

Reagents

Reagents used included GN Hajna broth (GN) from Difco containing sterile Hanks or RPMI 640 medium (RPMI) at a pH of about 7.2, heparinized tubes for drawing blood, kanamycin at 1 mg/mL in Hanks or RPMI, gentamicin at 10 ug/mL in Hanks or RPMI, MacConkey agar (Difco) and a sterile solution of 1% saponin in deionized water.

Methods

On day 1, an isolated colony of the wild-type strain was grown overnight in GN. On day 2, the following steps were performed. Approximately 5 mL of blood were drawn from a chicken into a heparinized tube. To this tube, 4 mL of sterile Hanks and 1 mL of the overnight inoculum (at a density of approximately 0.2 O.D. in growth medium at 595$\lambda$ in McFarland nephelometer) were added. The tube was incubated at 41° C. for 30 min with gentle stirring or slow rotation. 1 mL of kanamycin solution in Hanks was added to the 10 mL of solution in the tube. The tube was then incubated at 41° C. for 60 min and centrifuged at low speed (200 g) for about 10 min. 1 mL of the supernatant was inoculated in GN (wash #1) and also plated on MacConkey agar (plate #1). The residual supernatant was removed from the tube and 10 mL of gentamicin in Hanks were used to resuspend the pellet. The tube was then incubated for 30 min and centrifuged at low speed (200 g) for 10 min. 1 mL of the supernatant was inoculated in GN (wash #2) and also plated on a MacConkey agar plate (plate #2). The residual supernatant was removed and the pellet was resuspended in 20 mL of Hanks. The tube was then incubated for 30 min and centrifuged at low speed (200 g) for 10 min. 1 mL of the supernatant was inoculated in GN (wash #3) and also plated on a MacConkey agar plate (plate #3). The residual supernatant was removed and 2–3 drops of 1% saponin were added to the cell pellet and the tube vortexed. Then, 2 mL of Hanks was added followed by drop-plating 6 drops of the resulting suspension on a MacConkey agar plate (plate #4). 25 mL of GN were added to the tube and the tube was incubated overnight at 41° C.

On day 3, the 1st, 2nd and 3rd washes were inspected for sterility. If all washes were sterile, a single colony from plate #4 was subcultured in GN and blood agar in order to obtain isolated colonies. On day 4, an isolated colony was selected and inoculated into GN.

The heterophil adaptation protocol of day 2 through day 4 was repeated using heparinized blood from the same bird obtained by sequential bleeding until at least 5 heterophil passages were accomplished with sterile washes. The adaptation thus represents the interaction of single clone of SE and the phagocytic cells of an individual bird. In all of the heterophil passages, special precautions were taken to avoid accidental isolation of non-phagocytosed SE. The heterophil adaptation is considered successful if the number of SE colonies recovered after saponin lysis of heterophils diminishes gradually from dozens of colonies after the first passage to about 2–5 colonies in the six drops of lysed blood plated on MacConkey agar.

EXAMPLE 2

Bacteriologic Cultures of Feces and Eggs

Chicken feces was cultured according to techniques described by Bichler et al., *Am. J. Vet. Res.* 57:489–495 (1996); Gast R. K., *Poultry Science* 8:1611–1614 (1993). Briefly, feces was cultured overnight in trypticase soy broth, subcultured in tetrathionate broth with iodine and sulfadiazine for 2 days, subcultured in Rappaport-Vassiliadis medium, and plated on brilliant green agar. Salmonella-suspect colonies were identified by the KSU technique (Difco), and by slide agglutinability of a bacterial suspension in Salmonella D1 grouping serum (Difco). Eggs were cultured according to a modification of the method of Bichler et al., *Am. J. Vet. Res.* 57: 489–495 (1996). Briefly, the egg shell wash was followed by alcohol sterilization of the egg shell, then by separately culturing the inner egg shell membrane, the yolk and the white.

EXAMPLE 3

Procedures for Laying Hen Experiments

All laying hen experiments described below were carried out with mature (1–2 years old) Leghorn laying hens. The individually caged hens were selected for high egg production and sampled five times for absence of fecal and egg Salmonella infection (using culture methods as set out in Example 2) prior to selection into the experimental pool. The experimental SE strains (wild-type and heterophil-adapted SE strain (HASES) vaccine strains) were given in the drinking water. The drinking water was placed in cups, with one cup per cage. Feces was sampled from the collection trays once daily, and eggs were collected, refrigerated and cultured for SE (as described in Example 2) within 24 hours of collection. Challenge SE strains and HASES vaccine strains were not separately identified. The next treatment (vaccine or challenge) was not given until the feces and eggs of all hens were negative for SE for a minimum of 10 days.

EXAMPLE 4

Safety and Efficacy of HASES SETK499

HASES SETK499 vaccine strain was derived from wild-type field strain SETK474. HASES SETK499 was 5X heterophil-adapted as described in example 1.

Experiment SE1 was carried out in five cycles.

Cycle 1: 12 hens were exposed on each of 3 consecutive days to approximately $1 \times 10^8$ colony forming units (CFU's) of wild-type strains SETK474 and SETK584 in 50 mL of drinking water to determine frequency and duration of fecal shedding, and egg transmission of wild-type strains. 1 mL of $1 \times 10^8$ CFU's/mL was diluted into 50 mL of deionized drinking water. Drinking cups were not emptied or replaced until the hens drank all the water (usually 3–4 hours). Feces and eggs were cultured for SE recovery for 39 days.

Cycle 2: Cycle 2 was started 60 days after the beginning of Cycle 1. The 12 hens were re-exposed on two consecutive days to approximately $1 \times 10^8$ CFU's/50 mL of deionized drinking water of wild-type strains SETK474 and SETK584 (FIG. 1) in order to determine the possible existence of convalescent immunity on fecal shedding and egg transmission upon subsequent infection with the same strains.

Figure 2:
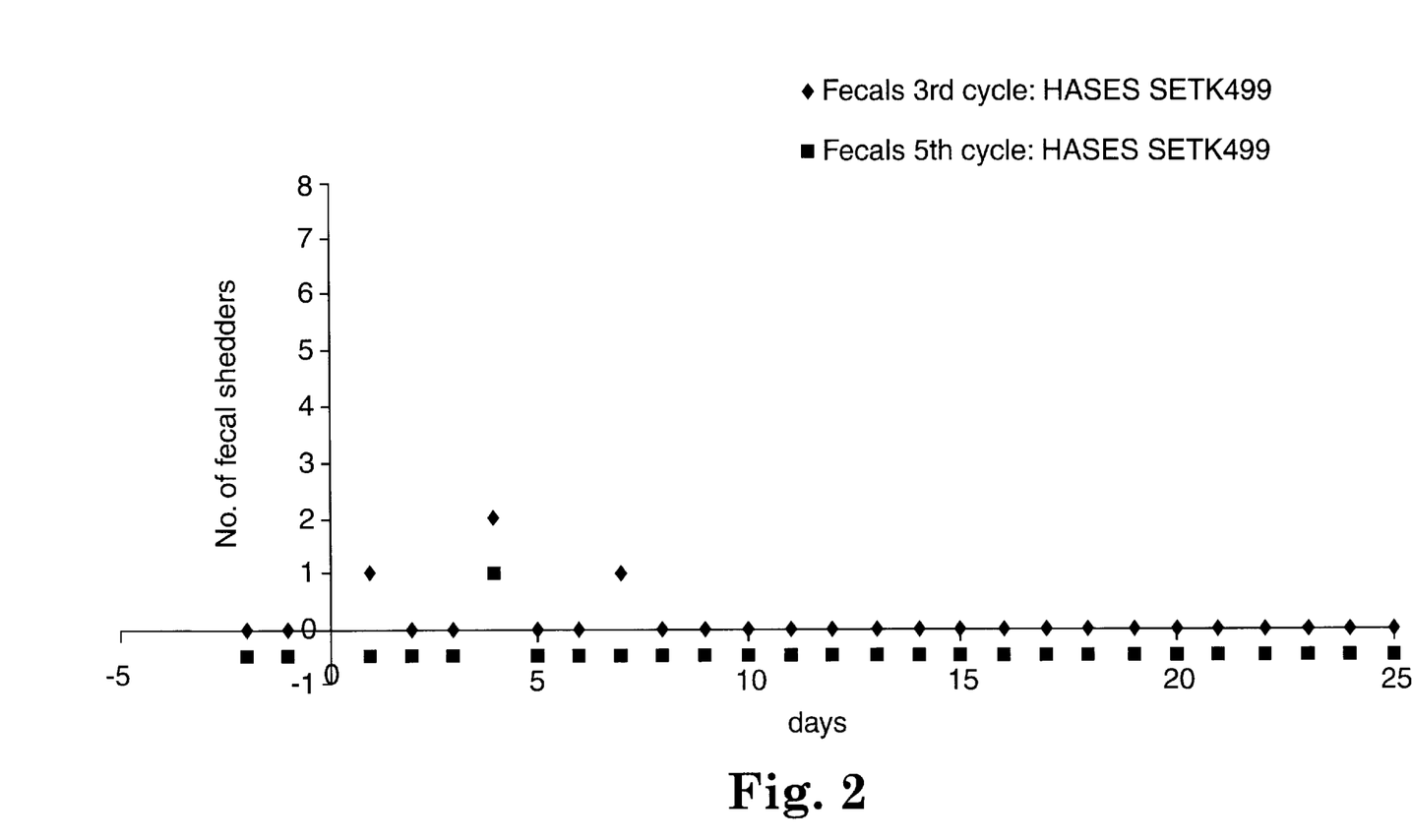
FIG. 2 depicts fecal shedding of vaccine strain HASES SETK499 (Experiment SE1).

Cycle 3: Cycle 3 was started 60 days after the beginning of Cycle 2. These hens were exposed on each of 3 consecutive days to $1 \times 10^8$ CFUs/50 mL of drinking water of HASES vaccine strain SETK499 (FIG. 2). Feces and eggs were sampled for 25 days after exposure to determine frequency and duration of fecal shedding, and egg transmission of the vaccine strain.

Figure 3:
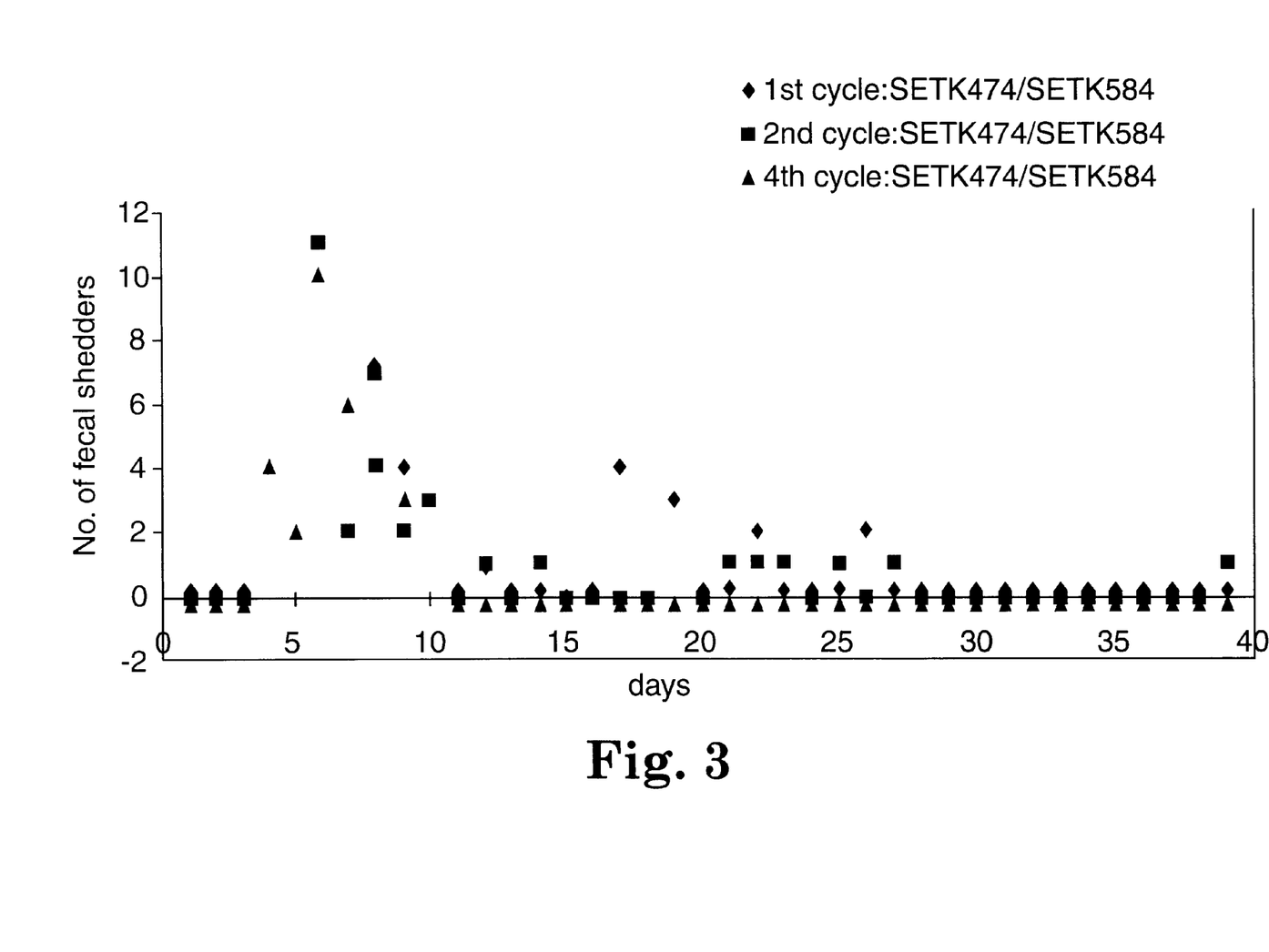
FIG. 3 depicts fecal shedding in experiment SE1 of SE wild-type challenge strains SETK474 and SETK584 before and after exposure to vaccine strain HASES SETK499.

Cycle 4: Cycle 4 was started 62 days after the beginning of Cycle 3. The hens were re-exposed on 2 consecutive days to $1 \times 10^8$ CFUs/50 mL of drinking water of wild-type strains SETK474 and SETK584 (FIG. 3). Feces and eggs were sampled for 39 days after exposure to determine frequency and duration of fecal shedding, and egg transmission of the challenge strain after vaccination (cycle 3) of hens.

Cycle 5: Cycle 5 was started 70 days after the beginning of Cycle 4. The hens were re-exposed to $1 \times 10^8$ CFUs/50 mL of drinking water of HASES SETK499 (FIG. 2) to determine the effect of anamnestic immunity on frequency and duration of fecal shedding and egg transmission.

Results and Discussion

Figure 1:
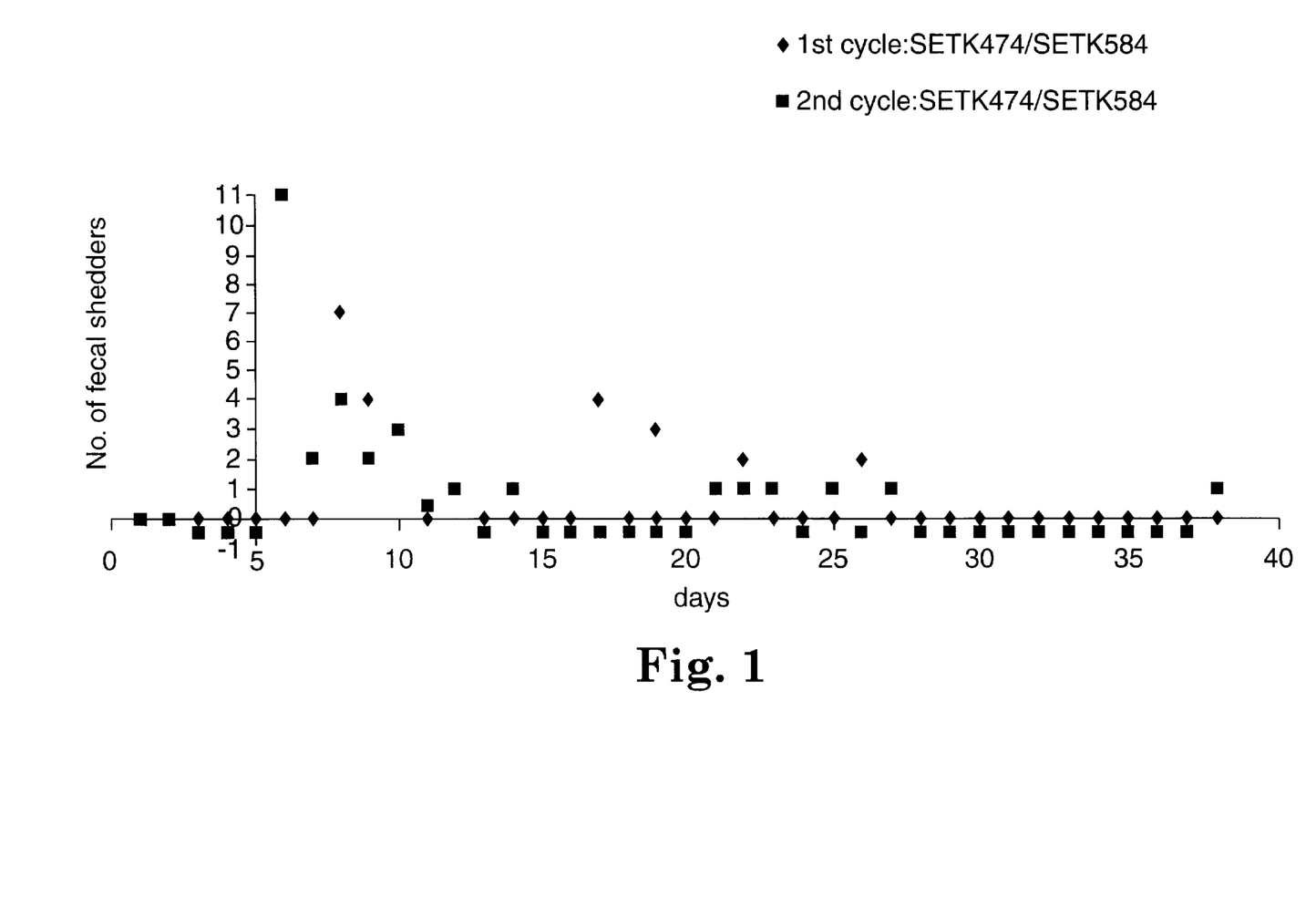
FIG. 1 depicts fecal shedding of SE wild-type challenge strains SETK474 and SETK584 (Experiment SE1).

The portions of the experiment encompassing cycles 1, 2 and 4 established that wild-type strains SETK474 and SETK584 were valid challenge strains for subsequent studies. The experiments established that challenge with these strains led to prolonged (>25 days post infection) fecal shedding (FIGS. 1 and 3), as well as egg transmission (6.6% to 9.2% of eggs were contaminated; Table 1). By way of comparison, the contamination rate in naturally SE-infected flocks varies from 0.05% to 0.5%. Experiment SE1 also revealed that prior exposure to these strains does not lead to convalescent immunity against fecal excretion (FIG. 1 and Table 1). While prior exposure to wild-type strains did not lead to immunity against fecal excretion, it may lead to partial immunity against egg transmission. Egg transmission in fact decreased in subsequent infection cycles (data not shown).

The procedures performed in cycles 3 and 5 were designed to establish that the 5X heterophil-adapted strain HASES SETK499 was shed at low frequency and for only a short time in feces (FIG. 2). When HASES SETK499 was given at $2 \times 10^8$ CFU on each of 3 subsequent days (cycle 3), fecal shedding occurred on only 3 occasions, on the first (1 hen), fourth (2 hens), and 7th (1 hen) days post-infection. Subsequent exposure, 34 days after cessation of shedding, to HASES SETK499 (5th cycle) resulted in only 1 hen shedding once on day 4 post-infection (FIG. 2). When hens were challenged with wild-type strain after cycle 3 vaccination, shedding of challenge strain ceased on day 10 post-infection.

The procedures of cycles 3 and 5 were also designed to establish that the heterophil-adapted strain is not transmitted to the egg. Neither HASES SETK499, nor subsequently administered challenge strain SETK584, were transmitted to the eggs of these hens (Table 1).

In summary, experiment SE1 revealed that HASES SETK499 is a safe and effective vaccine strain. The strain is shed in feces of infected hens at low frequency for only a short time after oral administration (7 days; cycle 3). Shedding was further reduced in frequency and duration upon 2nd infection with this strain (cycle 5), suggesting an anamnestic effect. Primary vaccination (cycle 3) appeared to have eliminated the challenge strain infection on day 10 post-infection. (Cycle 4). HASES SETK499 was not transmitted to eggs and appeared to prevent subsequent egg transmission of the challenge strain SETK584.

EXAMPLE 5

Characterization and Efficacy of HASES SETK598

HASES SETK598 vaccine strain was derived from wild-type field strain SETK499 and was 6X heterophil-adapted as described in Example 1.

Experiment SE2 was carried out in two cycles.

Figure 4:
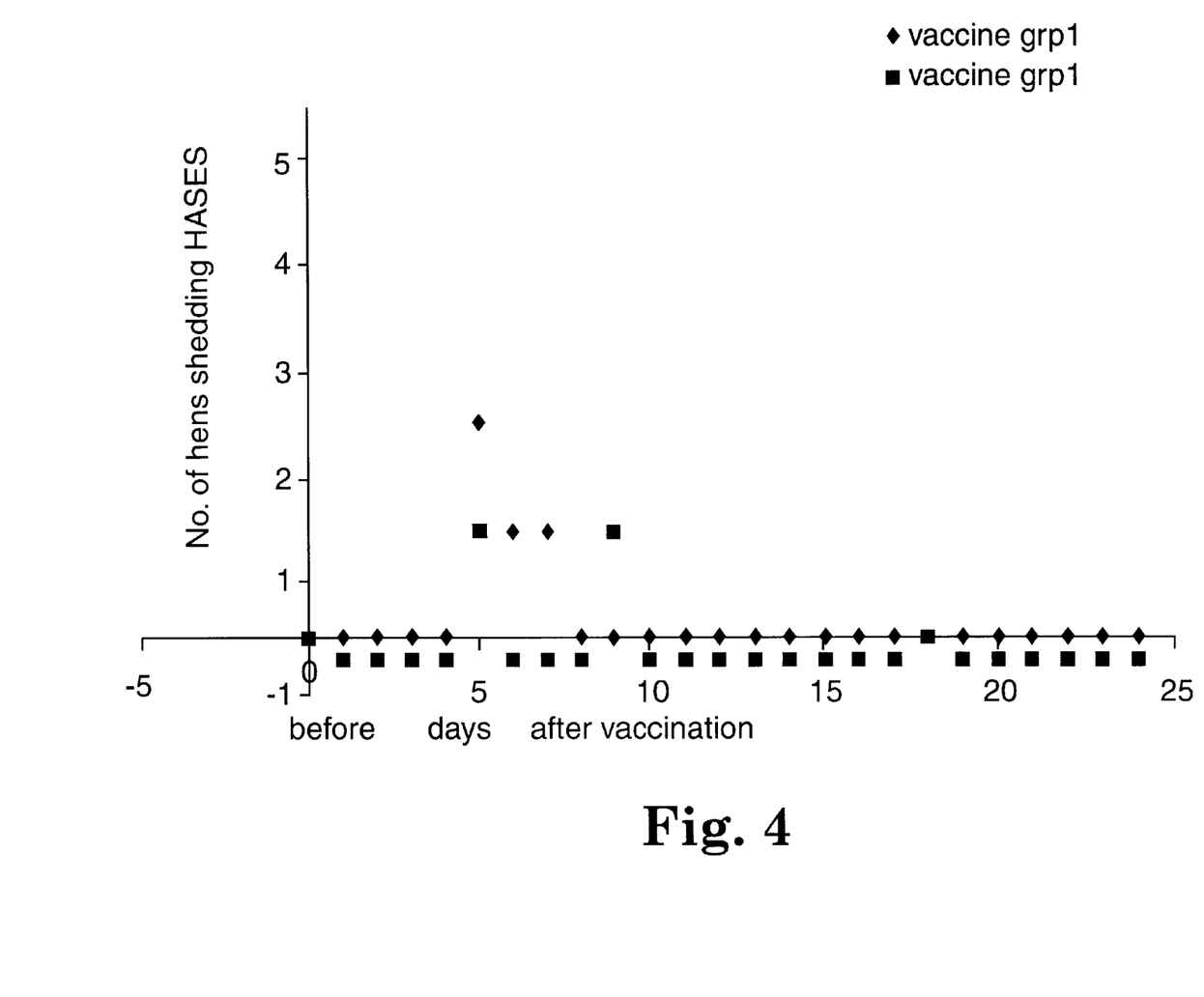
FIG. 4 depicts fecal shedding of vaccine strain HASES SETK598 (Experiment SE2).

Cycle 1 (Vaccine Safety): Ten hens (vaccine group 1) were repeatedly exposed to HASES SETK598 for primary and anamnestic immunizations. After administration of $3.40 \times 10^6$ CFUs of SETK598 in drinking water, feces and eggs were sampled for 24 days thereafter. The hens were re-exposed 45 days after the first exposure to $4.0 \times 10^6$ CFUs and samples were collected for 30 days. A third exposure of $5.0 \times 10^7$ CFUs initiated 30 days after the second exposure was performed in order to determine the frequency and duration of fecal shedding and egg transmission. Six hens (vaccine group 2) were treated in an identical manner, but were also given 50 ug cholera toxin (CT) in the drinking water on the days of vaccination. Cholera toxin was used because it is a known mucosal adjuvant of immunity (FIG. 4). The purpose of cycle 1 was to determine fecal shedding and egg transmission of HASES SETK598 upon repeated vaccination and to determine any effect of CT on subsequent immunity to challenge with wild-type field strain.

Cycle 2 (vaccine efficacy): Cycle 2 was started 65 days after the end of Cycle 1. The 16 immunized hens (vaccine groups 1 and 2, described above) were exposed to challenge strains. Approximately $1 \times 10^8$ CFUs of wild-type challenge strain SETK584 were given to these hens. Simultaneous identical challenge exposure of 11 control hens (FIG. 5) was performed to determine fecal shedding and egg transmission of challenge SE.

Results and Discussion

Figure 5:
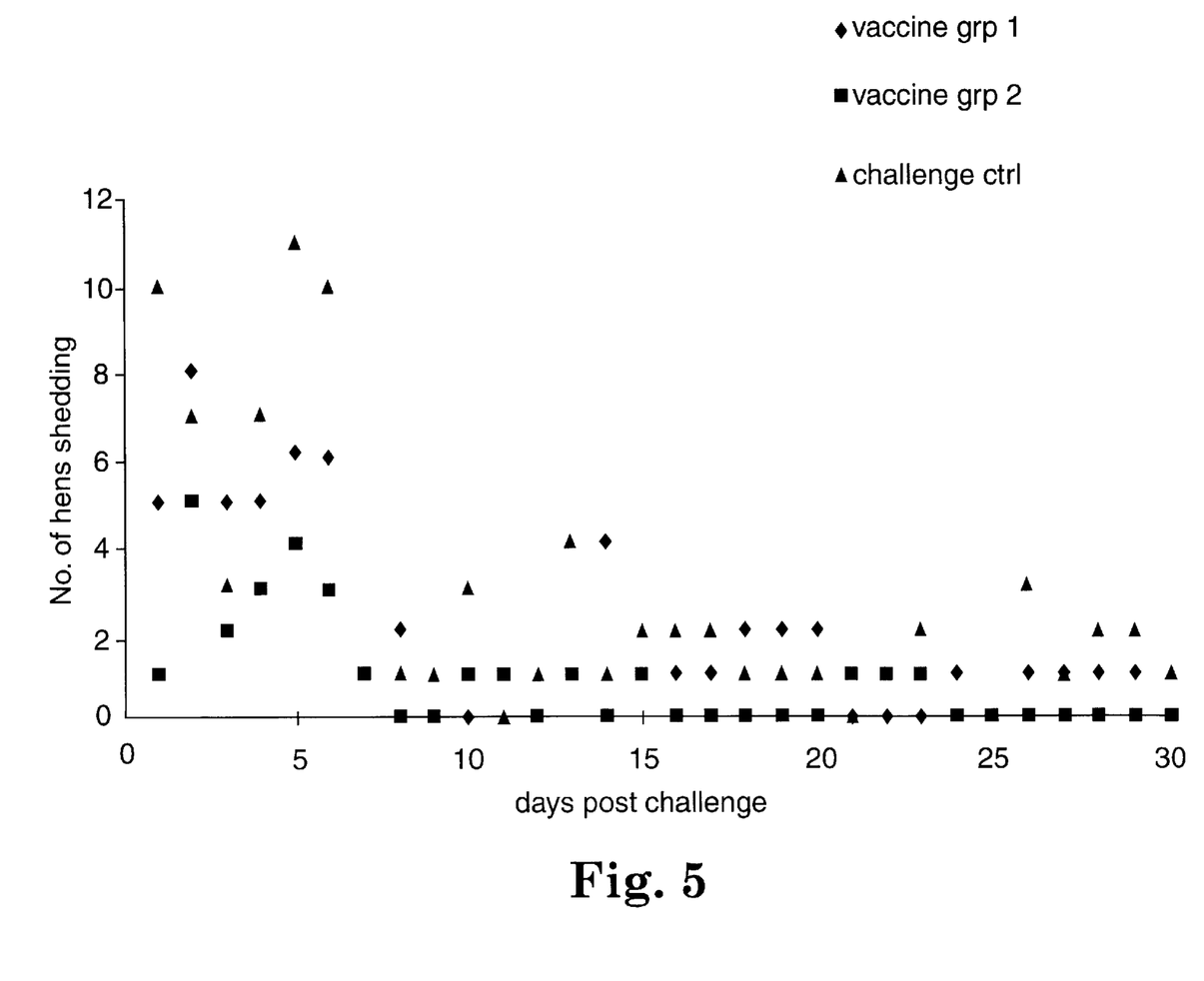
FIG. 5 depicts fecal shedding in vaccinated hens when challenged with wild-type strain SETK584 post vaccination (Experiment SE2).

Experiment SE2 reconfirmed the low and transient intestinal colonization of HASES, previously shown in experiment SE1 (See Example 4). Vaccination with HASES SETK598 was repeated three times, with 30-day or greater intervals between vaccinations. Salmonella was not isolated after the first and second low-dose vaccination cycles (at approximately $3$–$4 \times 10^6$ CFU per dose; data not shown). When HASES was given at a higher dose in a third immunization cycle ($5 \times 10^7$ CFU), it was recovered from 2 hens on day 5 post-infection, and from 1 hen on days 6 and 7 post-infection from group 1 vaccinated hens. Group 2 hens received 50 ug CT adjuvant with the vaccine, and HASES was recovered once only on day 5 post-infection, and once on day 9 post-infection. (FIG. 4). Fecal shedding of the challenge strain was significantly lower in vaccinated groups 1 and 2 than in the challenge control group (p<0.01; FIG. 5). Neither HASES nor the challenge SETK584 strain was isolated from any of 477 eggs of vaccinated groups 1 and 2, but were isolated from 4 of 71 eggs (5.6%) of the challenge control group (Table 1).

Experiment SE2 provided evidence that HASES SETK598 is not shed in feces of hens given approximately $10^6$ CFU repeatedly. It was shed from feces of a few hens for up to 9 days post-infection when given at a dose of $5 \times 10^7$ CFU. Repeated vaccinations with HASES SETK598 reduced the level of fecal shedding of the challenge strain in immunized hens. Neither the vaccine strain nor the challenge strain were found in eggs of vaccinated hens.

TABLE 1

Egg Infection with Wild-Type Strains SETK474 and SETK584 and Vaccine Strains HASES SETK499 and HASES SETK598

| Wild-type SETK474 and SETK584 | Eggs: No. infected/total | |
| --- | --- | --- |
| First challenge trial (SE1) | 4/61 | 6.6% |
| Second challenge trial (SE1) | 7/76 | 9.2% |
| Challenge trial (SE2) | 4/71 | 5.6% |
| Vaccine SE | | |
| 5X vaccine HASES SETK499 (SE1) | 0/244 | 0% |
| Challenge SE | 0/234 | 0% |
| 6X vaccine HASES SETK598 (SE2) | 0/250 | 0% |
| Challenge SE | 0/227 | 0% |

What is claimed is:

1. An isolated poultry heterophil-adapted strain of microorganism, wherein said poultry heterophil-adapted strain exhibits a genetic or biochemical change relative to a wild-type strain from which said poultry heterophil-adapted strain is derived.

2. The strain of claim 1, wherein said poultry heterophil-adapted strain is a member of the genus Salmonella.

3. The strain of claim 2, wherein said member is *Salmonella enteritidis*.

4. The strain of claim 1, wherein said poultry heterophil-adapted strain lacks a virulence plasmid.

5. The strain of claim 1, wherein said poultry heterophil-adapted strain is arginine hydrolase negative.

6. The strain of claim 1, wherein said poultry heterophil-adapted strain is alive.

7. The strain of claim 1, wherein said poultry heterophil-adapted strain is avirulent to a poultry species.

8. The strain of claim 7, wherein said poultry species comprises a species selected from the group consisting of a turkey, guinea, fowl, pigeons, quail, partridge, broiler chicken, and laying hen.

9. The strain of claim 1, wherein said poultry heterophil-adapted strain is in the form of a culture, frozen sample, lyophilized sample, or agar stab.

10. The strain of claim 1, wherein said poultry heterophil-adapted strain is SETK598 having ATCC Accession Number 55770.

11. A vaccine comprising an isolated poultry heterophil-adapted strain of microorganism, wherein administration of said vaccine to a poultry species immunizes said poultry species, and wherein said poultry heterophil-adapted strain exhibits a genetic or biochemical change relative to a wild-type strain from which said poultry heterophil-adapted strain is derived.

12. The vaccine of claim 11, wherein said poultry heterophil-adapted strain is a member of the genus Salmonella.

13. The vaccine of claim 11, wherein said member is *Salmonella enteritidis*.

14. The vaccine of claim 13, wherein said administration reduces or prevents transmission of a *Salmonella enteritidis* to an egg of said poultry species.

15. The vaccine of claim 13, wherein said administration reduces or prevents feces shedding of a *Salmonella enteritidis* by said poultry species.

16. The vaccine of claim 11, wherein said poultry heterophil-adapted strain lacks a virulence plasmid.

17. The vaccine of claim 11, wherein said poultry heterophil-adapted strain is arginine hydrolase negative.

18. The vaccine of claim 11, wherein said poultry heterophil-adapted strain is alive.

19. The vaccine of claim 11, wherein said poultry heterophil-adapted strain is avirulent to said poultry species.

20. The vaccine of claim 11, wherein said poultry species comprises a species selected from the group consisting of a turkey, guinea, fowl, pigeons, quail, partridge, broiler chicken, and laying hen.

21. The vaccine of claim 11, wherein said poultry heterophil-adapted strain is in the form of a culture, frozen sample, lyophilized sample, or agar stab.

22. The vaccine of claim 11, wherein said poultry heterophil-adapted strain is SETK598 having ATCC Accession Number 55770.

23. The vaccine of claim 11, wherein said vaccine is suitable for oral administration.

24. The vaccine of claim 11, wherein said vaccine is in aqueous suspension.

25. The vaccine of claim 11, wherein said vaccine is in a unit dosage form and said unit dosage is about $10^6$ to about $10^8$ colony forming units of said poultry heterophil-adapted strain.

26. The vaccine of claim 11, wherein said vaccine further comprises a mucosal adjuvant.

27. The vaccine of claim 26, wherein said mucosal adjuvant comprises cholera toxin.

* * * * *